US008328720B2

(12) United States Patent
Mir et al.

(10) Patent No.: US 8,328,720 B2
(45) Date of Patent: Dec. 11, 2012

(54) MEMS INTERSTITIAL PROTHROMBIN TIME TEST

(75) Inventors: Jose Mir, Rochester, NY (US); Marek W. Kowarz, Henrietta, NY (US); Kamal K. Sarbadhikari, Geneseo, NY (US); Philip Ryan Ashe, Rochester, NY (US)

(73) Assignee: Infotonics Technology Center, Inc., Canandaigua, NY (US)

( * ) Notice: Subject to any disclaimer, the term of this patent is extended or adjusted under 35 U.S.C. 154(b) by 1066 days.

(21) Appl. No.: 12/189,509

(22) Filed: Aug. 11, 2008

(65) Prior Publication Data
US 2009/0093697 A1    Apr. 9, 2009

Related U.S. Application Data

(60) Provisional application No. 60/955,054, filed on Aug. 10, 2007.

(51) Int. Cl.
*A61B 5/1459* (2006.01)
(52) U.S. Cl. ..................................... 600/369
(58) Field of Classification Search .................. None
See application file for complete search history.

(56) References Cited

U.S. PATENT DOCUMENTS

| | | | |
|---|---|---|---|
| 4,862,894 A | 9/1989 | Fujii | |
| 4,871,351 A | 10/1989 | Feingold | |
| 5,054,896 A | 10/1991 | Margolis | |
| 5,097,810 A | 3/1992 | Fishman et al. | |
| 5,099,857 A | 3/1992 | Baldo et al. | |
| 5,457,041 A | 10/1995 | Ginaven et al. | |
| 5,680,858 A | 10/1997 | Hansen et al. | |
| 5,741,211 A | 4/1998 | Renirie et al. | |
| 5,928,268 A | 7/1999 | Butwell et al. | |
| 5,971,963 A | 10/1999 | Choi | |
| 6,024,925 A | 2/2000 | Little et al. | |
| 6,355,054 B1 | 3/2002 | Neuberger | |
| 6,540,675 B2 | 4/2003 | Aceti et al. | |
| 6,692,456 B1 | 2/2004 | Eppstein et al. | |
| 6,887,202 B2 | 5/2005 | Currie et al. | |
| 6,923,764 B2 | 8/2005 | Aceti et al. | |
| 6,934,438 B2 | 8/2005 | Hoke | |
| 7,004,928 B2 | 2/2006 | Aceti et al. | |
| 7,132,054 B1 | 11/2006 | Kravitz et al. | |
| 7,585,578 B2 | 9/2009 | Yonekura et al. | |
| 2002/0002326 A1 | 1/2002 | Causey, III et al. | |
| 2002/0013849 A1 | 1/2002 | Schweitzer et al. | |
| 2002/0087056 A1 | 7/2002 | Aceti et al. | |
| 2003/0083680 A1 | 5/2003 | Jousson | |
| 2003/0083686 A1 | 5/2003 | Freeman et al. | |
| 2003/0153900 A1 | 8/2003 | Aceti et al. | |
| 2003/0208113 A1 | 11/2003 | Mault et al. | |
| 2003/0208167 A1 | 11/2003 | Prausnitz et al. | |
| 2003/0218756 A1 | 11/2003 | Chen et al. | |
| 2004/0096959 A1 | 5/2004 | Stiene et al. | |
| 2004/0138541 A1 | 7/2004 | Ward et al. | |
| 2004/0176701 A1 | 9/2004 | Fujii | |
| 2005/0070819 A1 | 3/2005 | Poux et al. | |
| 2005/0137536 A1 | 6/2005 | Gonnelli | |
| 2005/0171480 A1 | 8/2005 | Mukerjee et al. | |
| 2005/0182307 A1 | 8/2005 | Currie et al. | |
| 2005/0209565 A1 | 9/2005 | Yuzhakov et al. | |
| 2005/0228313 A1 | 10/2005 | Kaler et al. | |
| 2005/0228340 A1 | 10/2005 | Cleary et al. | |
| 2005/0256499 A1 | 11/2005 | Pettis et al. | |
| 2006/0002636 A1 | 1/2006 | Torre-Bueno et al. | |
| 2006/0047242 A1 | 3/2006 | Laurent et al. | |
| 2006/0049209 A1 | 3/2006 | Baker | |
| 2006/0094985 A1 | 5/2006 | Aceti et al. | |
| 2006/0219576 A1 | 10/2006 | Jina | |
| 2007/0092496 A1 | 4/2007 | Zheng et al. | |
| 2007/0100255 A1 | 5/2007 | Boecker et al. | |
| 2007/0110672 A1 | 5/2007 | Bellott et al. | |
| 2007/0276211 A1 | 11/2007 | Mir et al. | |

FOREIGN PATENT DOCUMENTS

| | | |
|---|---|---|
| DE | 19610293 C1 | 7/1997 |
| EP | 0299778 A2 | 1/1989 |
| EP | 1086718 B1 | 3/2001 |
| GB | 2309644 A | 8/1997 |
| WO | WO 01/80728 A1 | 11/2001 |
| WO | WO 03/092487 A1 | 11/2003 |

OTHER PUBLICATIONS

Milne et al., Am. J. Physiol., 189:470-474, 1957.*
Michel et al., J. Physiol., 501:657-662, 1997.*
Trautmann et al. (Transducers '05. The 13th International Conference on Solid-State Sensors, Actuators and Microsystems, 2005. Digest of Technical Papers.*
Tonnesen (Allergy, 41:196-202, 1986).*
Cula et al., "Bidirectional Imaging and Modeling of Skin Texture," Proceedings of Texture, Nice, France, 6 pages (Oct. 17, 2003).
Office Action from the United States Patent and Trademark Office for U.S. Appl. No. 11/995,366 (Apr. 29, 2010).
Schuster et al., "Macro-Video Documentation Patch Tests," Contact Dermatitis 52:177-83 (2005).
Ahn et al., "Micromachined Planar Inductors on Silicon Wafers for MEMS Applications," Dec. 1998, pp. 866-876, vol. 45, No. 6, IEEE Transactions on Industrial Electronics.
Alksne John F, "The Passage of Colloidal Particles Across the Dermal Capillary Wall Under the Influence of Histamine," Q J Exp Physiol Cogn Med Sci Jan. 1959; 44(1):51-66, http://www.unboundmedicine.com/medline/ebm/record/13624013/full_citation/The_passage_of_colloidal_particles_across_the_dermal_capillary_wall_under_the_influence_of_histamine_.

(Continued)

*Primary Examiner* — Brian J Gangle
(74) *Attorney, Agent, or Firm* — LeClairRyan, a Professional Corporation

(57) ABSTRACT

A method of determining a prothrombin time is disclosed. A mediator is applied to a stratum corneum. The stratum corneum is penetrated to allow the mediator to enter a region containing interstitial fluid and interact with at least one capillary, causing blood and/or blood components to leak from the at least one capillary into the region containing interstitial fluid. A characteristic affected by the blood and/or blood components is measured in the region containing interstitial fluid which correlates to the prothrombin time. A system for measuring prothrombin time is also disclosed. The system has a mediator, one or more microneedles, and a processor directly or indirectly coupled to the one or more microneedles and configured to determine a coagulation change in blood or blood components in a region around the one or more microneedles after the one or more microneedles penetrate a stratum corneum.

24 Claims, 12 Drawing Sheets

OTHER PUBLICATIONS

Baluk et al., "Endothelial Gaps and Adherent Leukocytes in Allergen-Induced Early- and Late-Phase Plasma Leakage in Rat Airways," American Journal of Pathology, Jun. 1998, vol. 152, No. 6, pp. 1463-1476, American Society for Investigative Pathology.

Damean et al., "Composite ferromagnetic photoresist for the fabrication of microelectromechanical systems," Oct. 2004, pp. 29-34; Journal of Micromechanics and Microengineering, Institute of Physics Publishing, 2005 IOP Publishing Ltd.

Dreborg, S., "Histamine reactivity of the skin," Allergy 2001:56, pp. 359-364, Munksgaard.

Grimes et al., "Magnetoelastic sensors for remote query environmental monitoring," Smart Mater. Strut. 8, Jun. 4, 1999, pp. 639-646, IOP Publishing Ltd., UK.

Ghidalia et al., "Overall Study of the in Vitro Plasma Clotting System in an Invertebrate, *Liocarcinus puber* (*Crustacea decapoda*): Considerations on the Structure of the Crustacea Plasma Fibrinogen in Relation to Evolution," Journal if Invertebrate Pathology, 1989, vol. 53, pp. 197-205, Academic Press, Inc.

Hunter et al., "Minimally Invasive Glucose Sensor and Insulin Delivery System," Phase 2 Final Report, Sep. 30, 2000, pp. 1-17, MIT Home Automation and Healthcare Consortium.

Litwiller, Dave, "CCD vs. CMOS: Facts and Fiction," Jan. 2001, pp. 1-4, issue of Photonics Spectra, Lauren Publishing Co., Inc.

Majno et al., "Endothelial Contraction Induced by Histamine-Type Mediators—An Electron Microscopic Study," The Journal of Cell Biology, Sep. 1, 1969, pp. 647-672, vol. 42.

Michel et al., "Microvascular Permeability," Physiological Reviews, Jul. 1999, vol. 79, No. 3, 60 pages.

Neal et al., "Transcellular gaps in microvascular walls of frog and rat when permeability is increased by perfusion with the ionophore A23187," Journal of Physiology 1995, vol. 488, No. 2, pp. 427-437.

Ong et al., "Magnetism-Based Remote Query Glucose Sensors," Sensors 2001, pp. 138-147, http://www.mdpi.net/sensors, MDPI, University Park, Pennsylvania.

Paquit et al., "Near-infrared imaging and structured light ranging for automatic catheter insertion," 2006, pp. 1-9, Oak Ridge National Laboratory, Oak Ridge, Tennessee.

Prinz et al., "Automatic Measurement of Skin Wheals Provoked by Skin Prick Tests," Connecting Medical Informatics and Bio-Informatics, 2005, pp. 441-446, IOS Press, EFMI, Vienna, Austria.

"Proximity Series: InfiniMini™," 2008, pp. 1-18, Infinity Photo-Optical Company, Boulder, Colorado.

Ramaswamy et al., "Microfluidic device and system for point-of-care blood coagulation measurement based on electrical impedance sensing," Nov. 2011, 7 pages, Sensors and Actuators B: Chemical, Elsevier B.V.

Ramaswamy et al., "Microfluidic Device to Perform Impedometric Detection of Activated Partial Thromboplastin Time of Blood," Jun. 5-9, 2011, pp. 222-225, Solid-State Sensors, Actuators and Microsystems Conference (Transducers).

Renkin, E.M., "Multiple pathways of capillary permeability," Circulation Research, 1977, vol. 41 pp. 735-743, American Heart Association Publication.

Sarin, Hemant, "Physiologic upper limits of pore size of different blood capillary types and another perspective on the dual pore theory of microvascular permeability," Journal of Angiogenesis Research 2010, 2:14.

Zhao et al., "Quantitative correlations among fibrinogen concentration, sedimentation rate, and electrical impedance of blood," Medical & Biological Engineering & Computing, May 1997, vol. 35, pp. 181-185.

Zhou et al., "Impedance Analysis of Blood Coagulation by Prothrombin Time Assay in a Miniature Device," Jun. 13-15, 2005, pp. 737-741, Paper No. ICMM2005-75155, 3rd International Conference on Microchannels and Minichannels (ICMM2005), ASME, Toronto, Ontario, Canada.

Burroughs, Chris, "Sandia—developed ElectroNeedles may give diabetes patients a way to painlessly check glucose levels," Sandia National Laboratories, LabNews, Jul. 22, 2005, vol. 57, No. 15, p. 5.

Zimmerman, Stefan, et al., "A Microneedle-Based Glucose Monitor: Fabricated on a Wafer-Level Using In-Device Enzyme Immobilization," The 12th International Conference on Solid State Sensors, Actuators and Microsystems, Boston, Jun. 8, 2003, p. 99-102.

"Debiotech received a Swiss Technology Award 2006 and the Vontobel Prize for its novel Insulin Pump and microneedle patch," Last accessed, Jun. 1, 2006, Debiotech.com/news, p. 1-3. (http://www.debiotech.com/news).

Kravitz, Stanley, H., et al., "A Quick, Reliable, and Versatile Method for Creating Microneedles for Bio-Harvesting," 2004 Joint International Meeting on Microfab., Oct. 4, 2004, Sandia National Laboratories, Albuquerque, NM.

Kuo, Shyh-Chyi, et al., "A Novel Polymer Microneedle Arrays and PDMS Micromolding Technique," Tamkang Journal of Science & Engineering, 2004, vol. 7 No. 2, p. 95-98.

Sony Corporation, "DFW-V500, DFW-VL500, Technical Manual (Ver.1.0)—English-," manual, 2001, p. 2-39, Sony Corporation.

Wang, Ping M., et al., "Minimally Invasive Extraction of Dermal Interstitial Fluid for Glucose Monitoring Using Microneedles," Diabetes Tech. & Therapeutics, 2005, vol. 7, No. 1. p. 131-142.

* cited by examiner

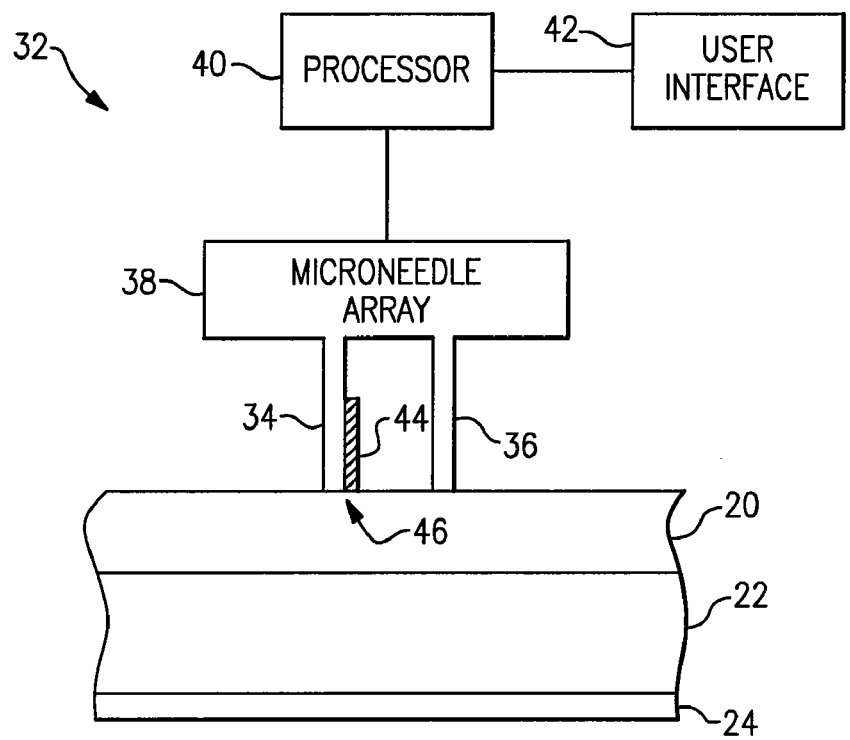
FIG.3A1
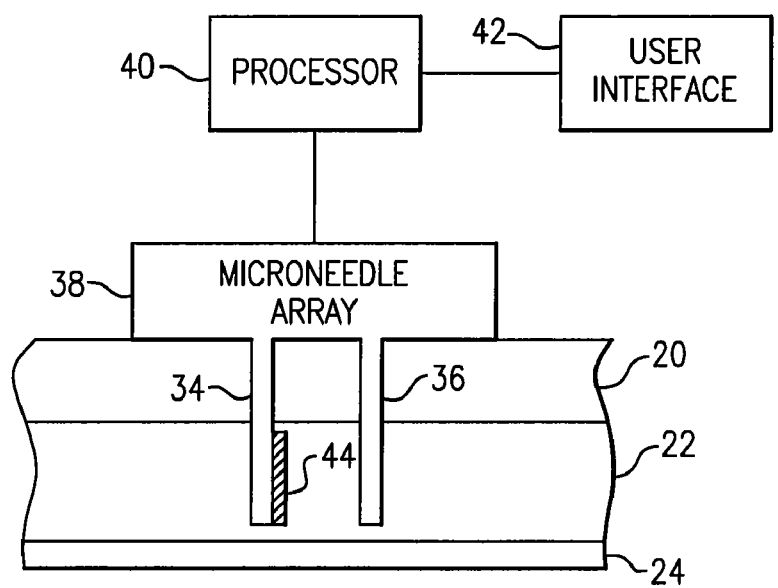
FIG.3B1

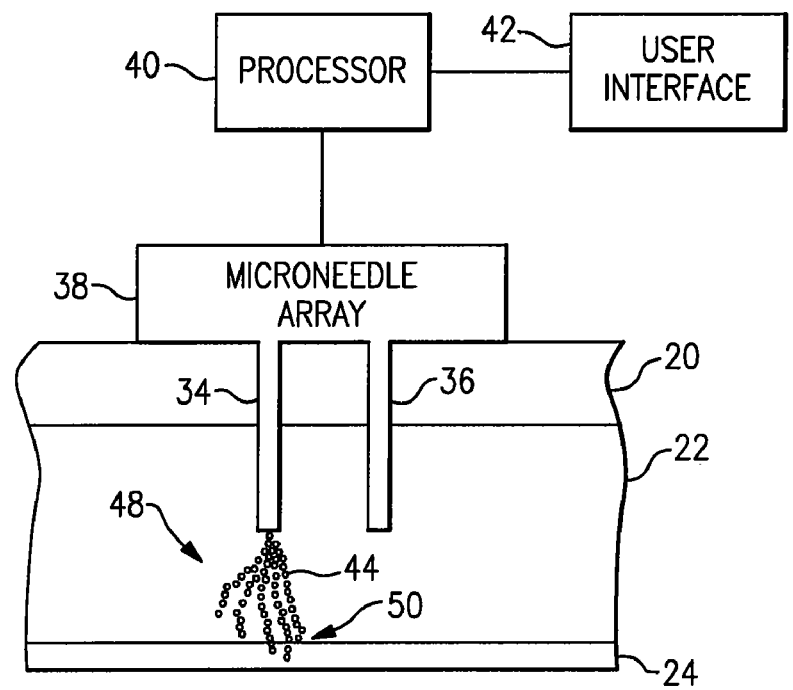
FIG.3C1
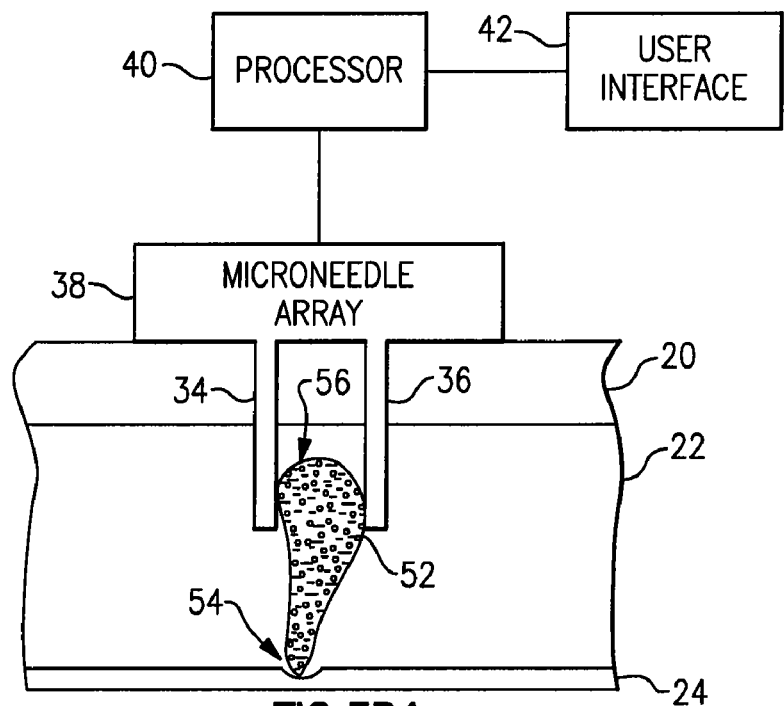
FIG.3D1

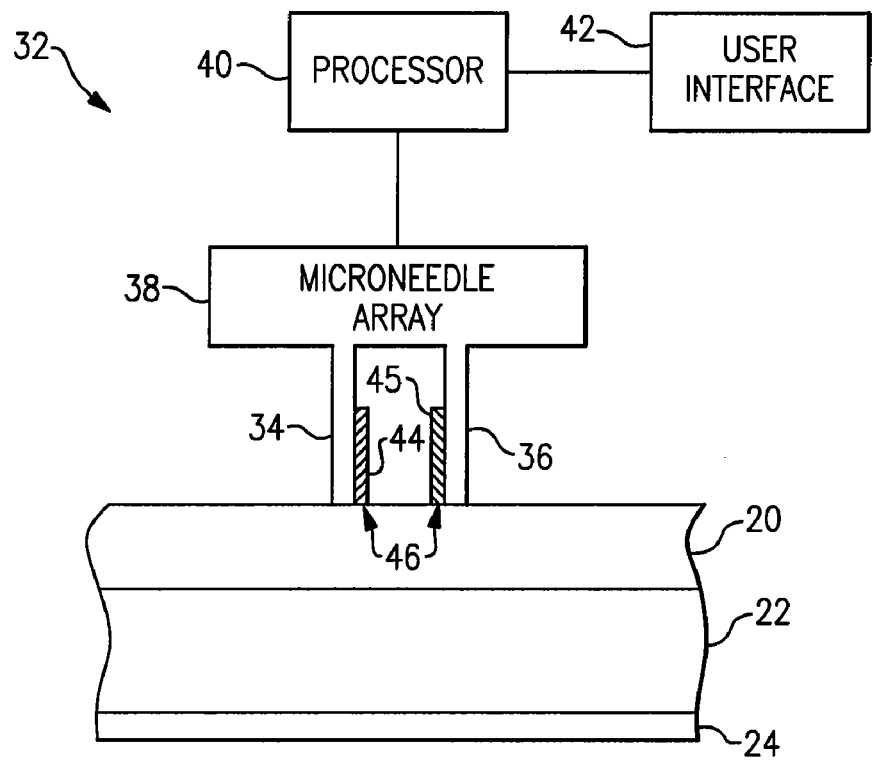
FIG.3A2
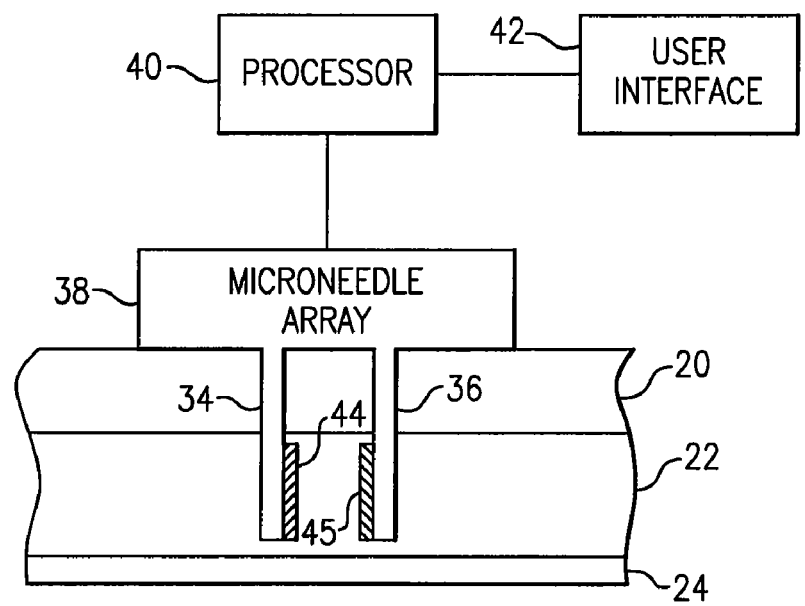
FIG.3B2

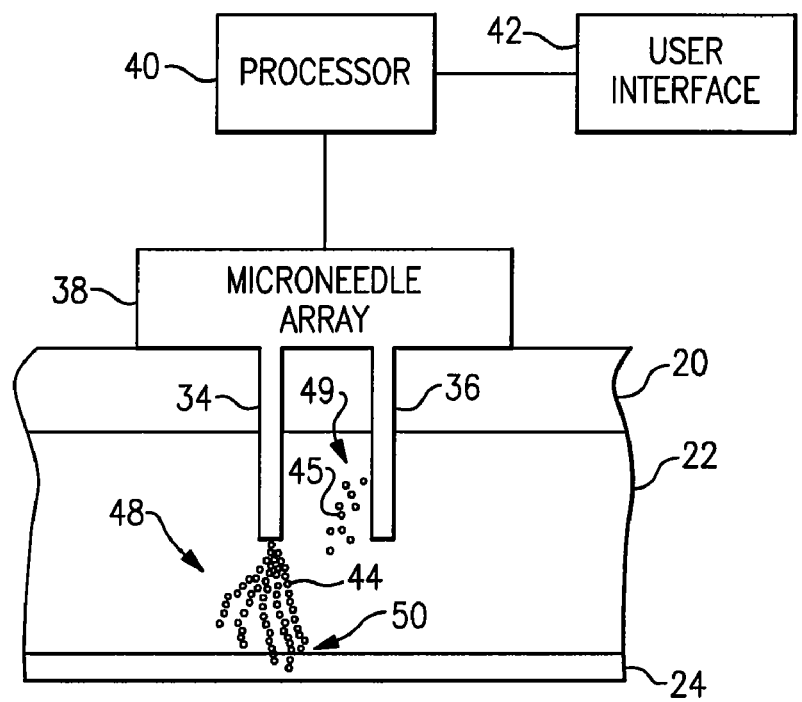
FIG.3C2
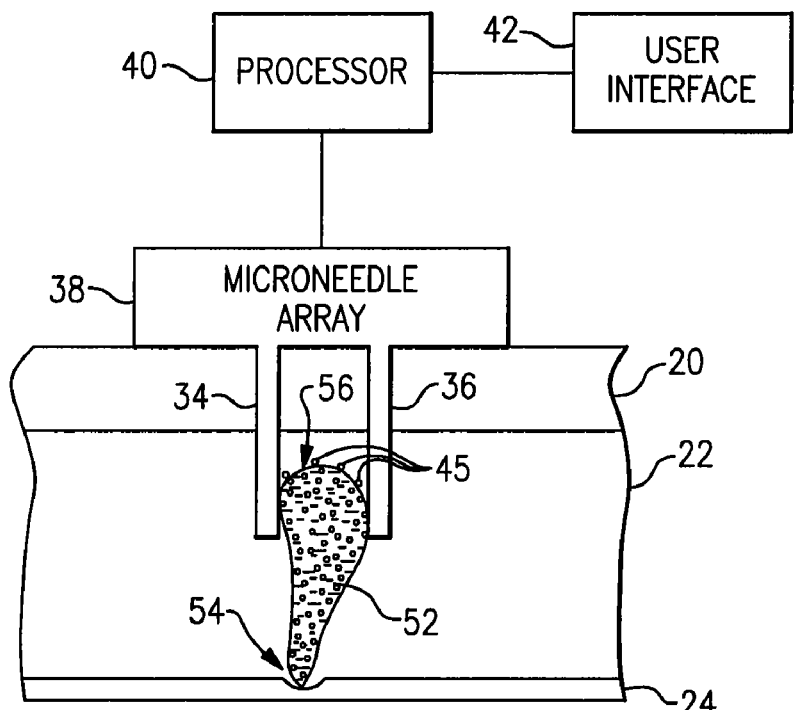
FIG.3D2

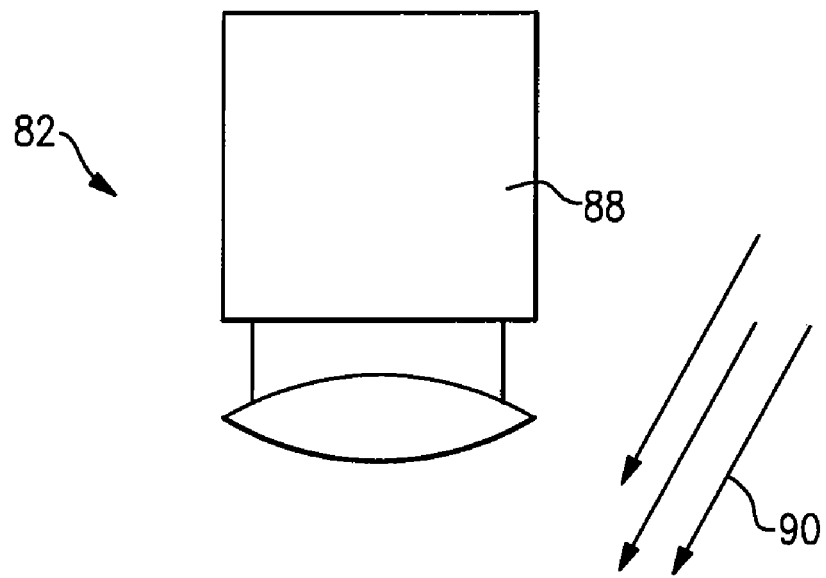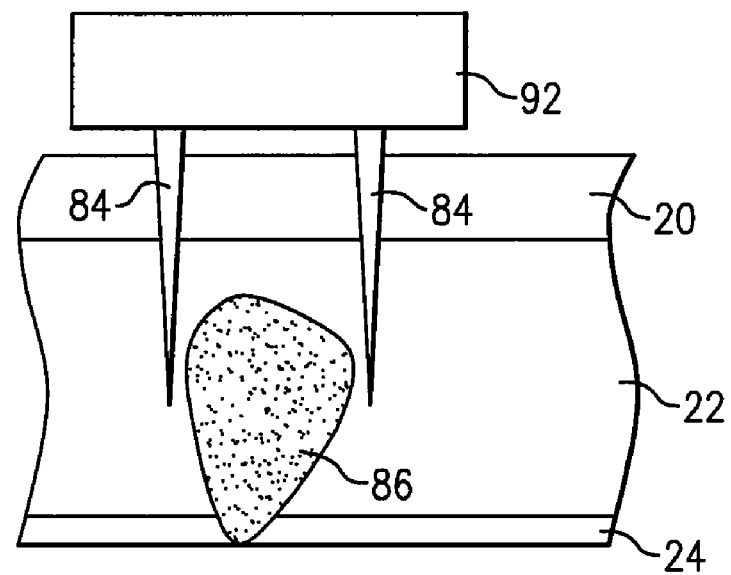
FIG. 7

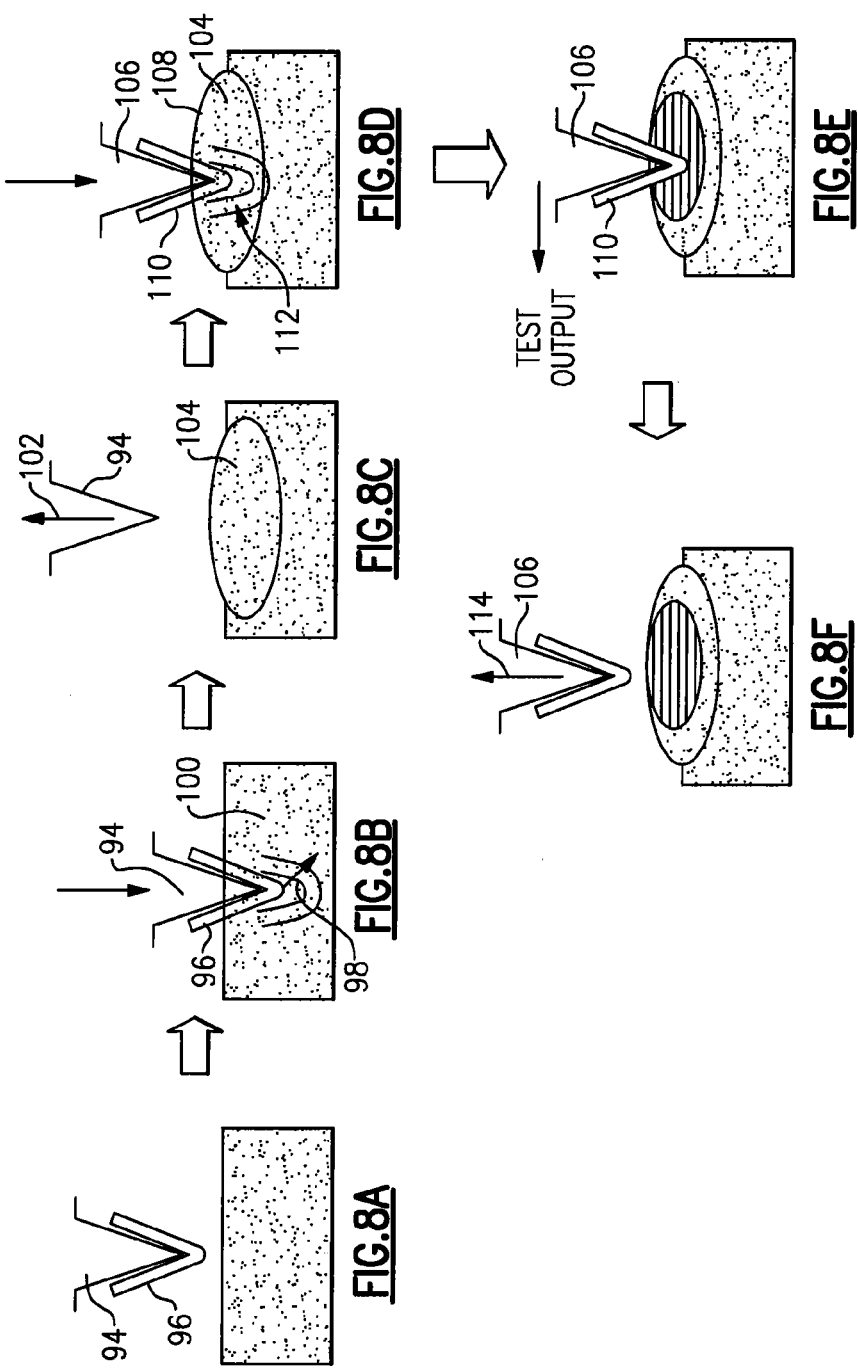

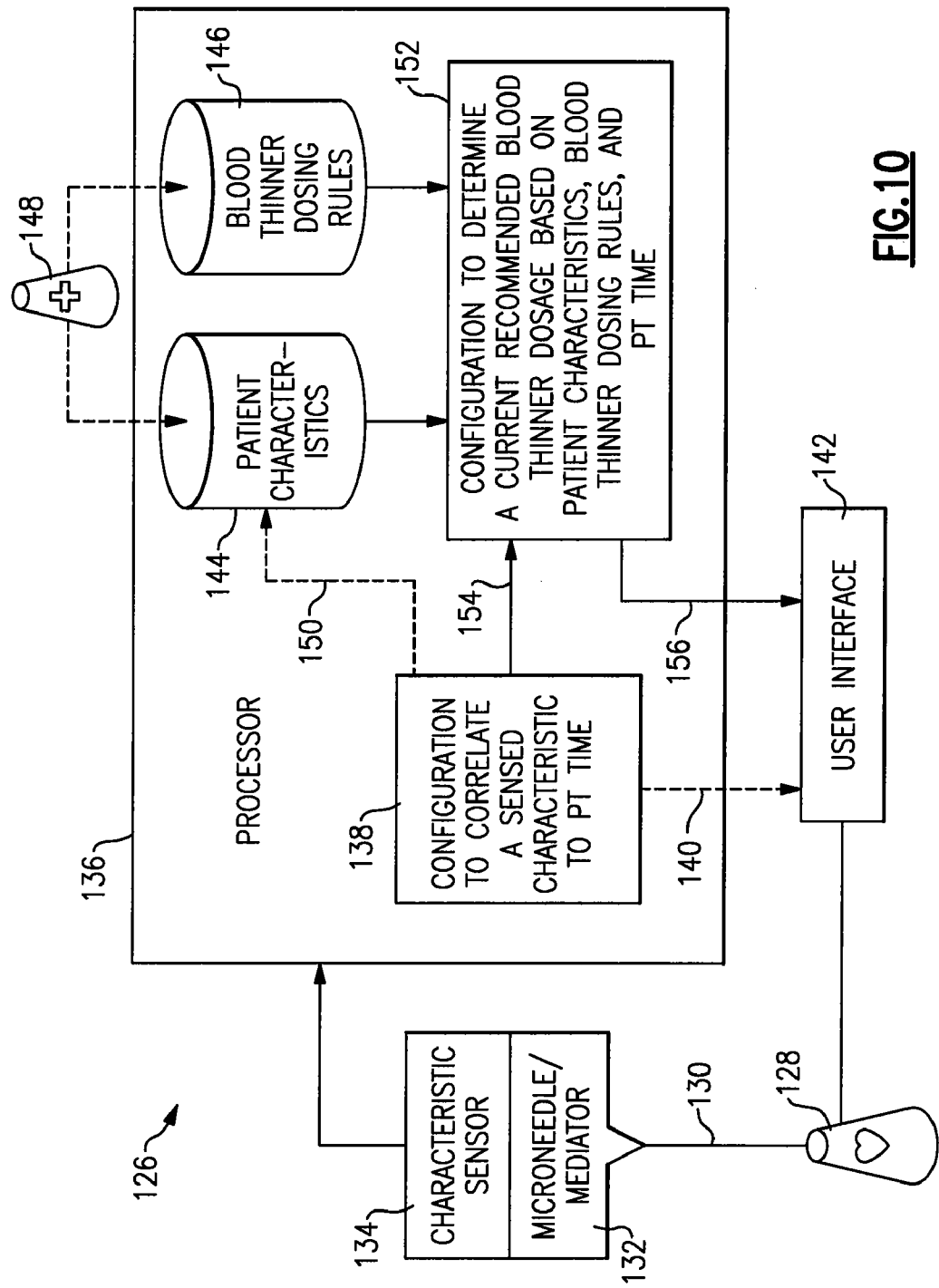

MEMS INTERSTITIAL PROTHROMBIN TIME TEST

RELATED APPLICATIONS

This application claims priority to U.S. provisional patent application 60/955,054 entitled, "MEMS INTERSTITIAL PROTHROMBIN TIME TEST" which was filed on Aug. 10, 2007. The provisional U.S. application 60/955,054 is hereby incorporated by reference in its entirety.

FIELD

The claimed invention generally relates to systems and methods for measuring prothrombin time and, more particularly, to a MEMS system and method for measuring prothrombin time.

BACKGROUND

Blood clotting, or coagulation, results from a sequence of reactions involving several proteins known as coagulation factors. Some of these factors have other names. For example, Factor I is also called fibrinogen, and Factor II is prothrombin. The liver produces these proteins and secretes them into the blood. Coagulation begins when some of the coagulation factors contact damaged tissue. Each factor reaction triggers the next reaction in a cascade. The final product of the coagulation cascade is a blood clot or a thrombus. The formation of a blood clot in a blood vessel (thrombosis) and its subsequent release (thromboembolism) can lead to grave medical conditions such as systemic embolism, stroke, and other blood clotting disorders.

Normally, the blood's ability to clot is a desirable characteristic. Some people, however, will develop conditions which may be negatively impacted by normal blood clotting. For example, people with certain types of irregular heart beat, people with prosthetic heart valves, or people who have suffered a heart attack are in danger of blood clots forming or growing larger in the blood and blood vessels. Such clots can lodge in the heart, lungs, or brain and cause strokes or even death in some cases. As treatment for people at risk of blood clotting disorders, physicians often prescribe oral anticoagulants such as warfarin or heparin. Other patients that can benefit from anticoagulants include cardiac patients, post-surgical patients, or trauma victims susceptible to thrombosis as a result of tissue and blood vessel damage. These patients are treated with anticoagulant therapy for a period of time after invasive surgery or trauma when they are most at risk.

The dosage of anti-clotting medication given to patients must be carefully determined. The anti-clotting medication is dosed based on the amount of clotting factors which are present in a person's blood. Coagulation can be strongly affected by diet or medication. For example, foods rich in vitamin K are well known to interact with the effects of prescribed anticoagulants. Variability in consumption of vitamin K containing foods such as green vegetables or vitamin supplements can deregulate the prescribed dosage, placing the patient in risk. The therapeutic range of blood coagulation is relatively narrow-outside this range, the patient can experience serious complications such as thromboembolism or, on the other extreme, hemorrhaging and internal bleeding. This problem is extensive in our society, leading to an estimated 300,000 deaths per year in the US alone.

A number of tests are performed in clinical laboratories to measure coagulation. Most are assays where the patient's blood is exposed to reagents that catalyze coagulation and thereafter, the time to reach a level of coagulation is monitored. The clotting time is then compared with a standard to obtain a relative ratio. The most widely used test of this type is the so-called prothrombin time assay or PT test. Unfortunately, due to the fact that coagulation agents such as fibrinogen are present primarily in blood, PT tests do not use other body fluids such as urine, interstitial, or lymph fluids. Consequently, coagulation testing is invasive and requires drawing blood. Although testing methods are improving that require lower blood volumes for analysis, all tests today require blood to be drawn.

As a result of fluctuations in clotting factors, patients on anti-coagulation therapy need to be routinely tested. Results from coagulation tests are of great value since they can provide preventive warning to the aforementioned complications and guide changes to the patient's dosage of oral anticoagulants. Depending on the stage and type of anticoagulant therapy, optimal test frequency can vary. Over ten million high risk surgical patients go on anticoagulation therapy in the US every year and are tested routinely at centralized laboratories associated with hospitals. Another three million people treated continuously with medication such as warfarin also require periodic testing. There is strong evidence that suggests coagulation testing every week or less can improve the ambulatory patient's ability to be within a safe therapeutic range. Due to the inconvenience of testing, however, testing compliance is often poor.

As mentioned, one type of coagulation test is called a prothrombin time (PT) test, which is a measure of the amount of time it takes blood to clot. Patients need to see a healthcare professional to have a PT test done. Blood must be drawn from the patient into a test tube, typically using a needle stick into a vein. The test tube usually contains an anticoagulant such as liquid citrate to keep the blood from coagulating prematurely. The blood sample is then mixed and centrifuged to separate blood cells from plasma. The plasma may then be analyzed on an instrument which takes a sample of the plasma. An excess of calcium is added to reverse the effect of the anti-coagulant, thereby enabling the blood to clot again. A tissue factor is added to simulate damaged tissue, and the time the sample takes to clot is measured optically. As a result of the number of skilled people who are involved in a PT test, as well as the equipment involved, the current prothrombin time (PT) test can be expensive. Additionally, a patient must often take the time to visit a laboratory for the test or coordinate a schedule with a visiting nurse. It can also take a significant amount of time to receive results from the test.

For an accurate prothrombin time measurement, the proportion of blood to citrate needs to be fixed. A preset amount of citrate (anticoagulant) is typically in each blood draw test tube. As a result, many laboratories will not perform the PT test if the sample tube of blood is underfilled. Therefore, in addition to being highly invasive, expensive, and time consuming, the PT test may require a relatively large sample of blood to be drawn each time the test is done.

Therefore, there is a need for a less expensive, less invasive, and more convenient prothrombin time test which encourages more frequent testing of blood clotting capability to assist health care professionals and patients in determining and adjusting the proper dosage of anti-clotting (or blood-thinning) medication. Such a test could also provide a more portable method used by the patient, in a point-of-care facility, or perhaps be administered directly by nursing staff or medical technicians.

SUMMARY

A method of determining a prothrombin time is disclosed. A mediator is applied to a stratum corneum. The stratum corneum is penetrated to allow the mediator to enter a region containing interstitial fluid and interact with at least one capillary, causing blood and/or blood components to leak from the at least one capillary into the region containing interstitial fluid. A characteristic affected by the blood and/or blood components is measured in the region containing interstitial fluid which correlates to the prothrombin time.

A system for measuring prothrombin time is also disclosed. The system has a mediator, one or more microneedles, and a processor directly or indirectly coupled to the one or more microneedles and configured to determine a coagulation change in blood or blood components in a region around the one or more microneedles after the one or more microneedles penetrate a stratum corneum.

A system for prescribing a dosage of blood thinner for a patient is further disclosed. The system has a mediator, one or more microneedles, and a processor directly or indirectly coupled to the one or more microneedles. The processor is configured to: 1) determine a coagulation change in blood or blood components in a region around the one or more microneedles after the one or more microneedles penetrate a stratum corneum; 2) store one or more patient characteristics; 3) store one or blood thinner dosing rules; and 4) determine a recommended blood thinner dosage based on the one or more patient characteristics, the one or more blood thinner dosing rules, and the determined coagulation change.

BRIEF DESCRIPTION OF THE DRAWINGS

FIGS. 3A1-3D1 schematically illustrate one embodiment of a system for monitoring prothrombin time and steps in the prothrombin time monitoring process.

FIGS. 3A2-3D2 schematically illustrate other embodiments of a system for monitoring prothrombin time and steps in the prothrombin time monitoring process.

FIG. 7 schematically illustrates another embodiment of a system for monitoring prothrombin time.

FIGS. 8A-8F schematically illustrate another embodiment of a system for monitoring prothrombin time and steps in the prothrombin time monitoring process.

FIG. 10 schematically illustrates a system for prescribing a dosage of a blood thinner based in part on a PT time determined from a sensor.

Figure 1:
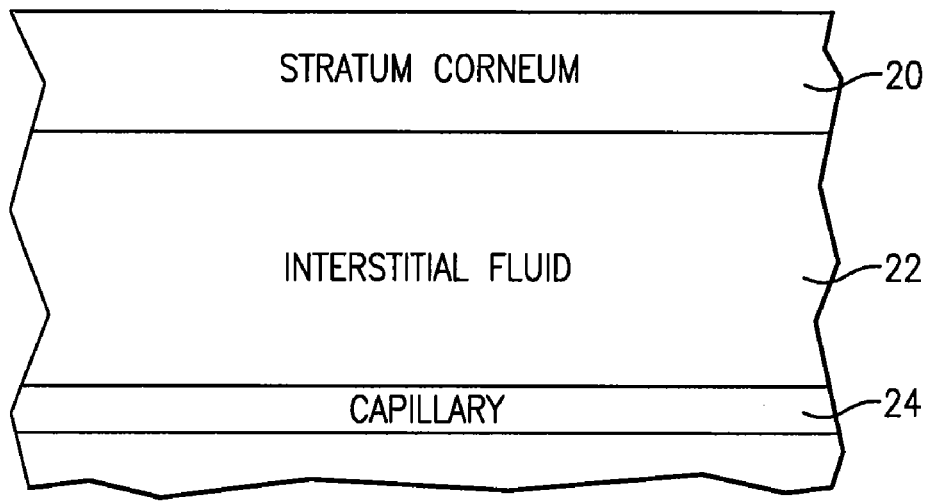
FIG. 1 schematically illustrates a side view cross-section of tissue.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

The outer layer of human skin is commonly referred-to as the epidermis. The outer-most layer of the epidermis is known as the stratum corneum. The stratum corneum is composed mainly of dead cells that lack nuclei. As these dead cells slough off, they are continuously replaced by new cells from layers below the stratum corneum. FIG. 1 schematically illustrates a side cross-sectional view of human skin tissue having the outer stratum corneum 20. Beneath the stratum corneum 20 are various layers of cells which are bathed and surrounded by interstitial fluid 22. Interstitial fluid 22 is a water solvent having amino acids, sugars, fatty acids, coenzymes, hormones, neurotransmitters, salts, and waste products from the cells.

The illustrated tissue in FIG. 1 also has at least one capillary 24 which carries blood through the tissue. The composition of interstitial fluid 22 depends on the exchanges between the cells in the tissue and blood. Not all of the contents of the blood pass into the tissue, which means that the interstitial fluid and the blood are not the same. Red blood cells, platelets, and plasma proteins cannot normally pass out of the walls of the capillaries 24 and into the interstitial fluid 22.

Figure 2A:
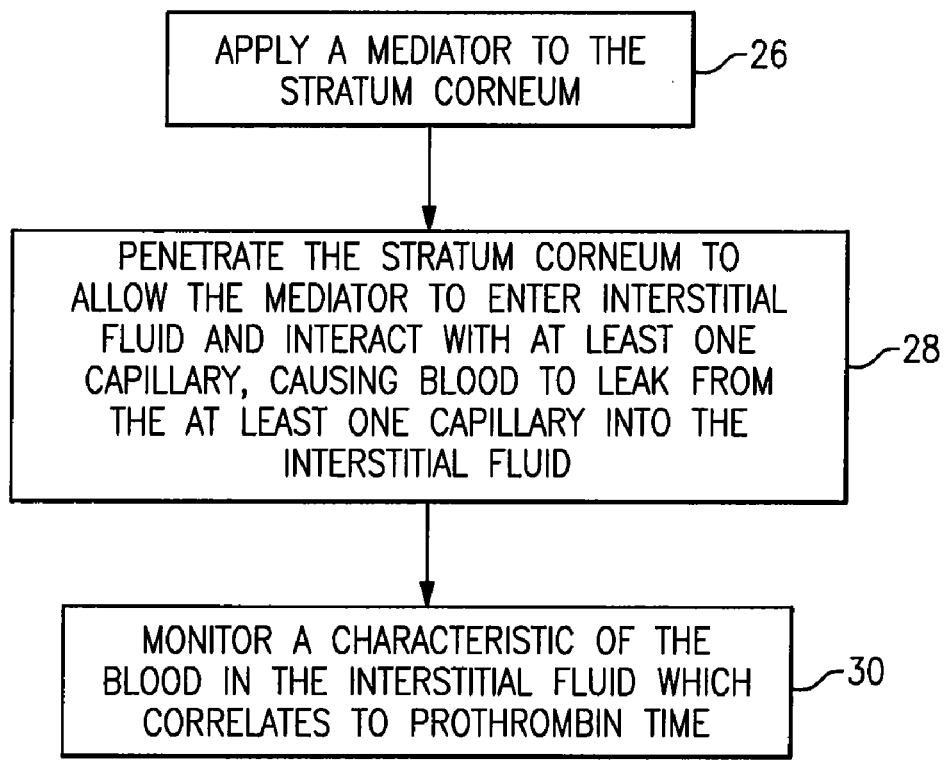
FIG. 2A illustrates one embodiment of a method of determining a prothrombin time.

FIG. 2A illustrates an embodiment of a method of determining a prothrombin time. A mediator is applied 26 to the stratum corneum 20. A mediator is a substance or structure that mediates a specific response in a bodily tissue. As used here, the mediator is a substance which is configured to increase microvascular permeability when contacting the at least one capillary 24, thereby allowing blood components such as plasma, proteins, macromolecules, and blood cells to leak out of the at least one capillary 24 into the region containing interstitial fluid 22. The mechanism responsible for this phenomenon is believed to be the creation of gaps in capillary walls caused by contraction of endothelial cells composing the capillary walls.

The mediator may be applied 26 to the stratum corneum 20 in a variety of ways. For example, the mediator may be applied in a liquid form to the stratum corneum 20. The mediator may also be applied to the stratum corneum 20 by touching a microneedle coated with the mediator to the stratum corneum 20. Alternatively, the mediator may be dry coated or liquid-coated onto the microneedle.

Next, the stratum corneum 20 is penetrated 28 to allow the mediator to enter the region containing interstitial fluid 22 and interact with at least one capillary 24, causing blood and/or blood components to leak from the at least one capillary 24 into the region containing interstitial fluid 22. At least one microneedle may be used to penetrate the stratum corneum 20. The microneedle may be preferably sized to penetrate the stratum corneum 20 while not extending down into nerve tissue in order to minimize the discomfort and pain for a subject. In some embodiments, the microneedle may cause minor damage to local capillaries resulting in additional leakage of blood components such as plasma, proteins, macromolecules, and blood cells. A microneedle may have a height of about 50-1000 microns and a tip dimension from submicron to about 80 microns in order to penetrate a subject's skin, although other embodiments may have other dimensions. Other embodiments may use other penetrating devices besides a microneedle.

The mediator is chosen to interact with the at least one capillary 24 to cause blood and/or blood components to leak from the at least one capillary 24. The mediator can do this, for example, by increasing the microvascular permeability of the capillary walls. One example of a suitable mediator which may have this effect is histamine. Other suitable examples of mediators may be serotonin, norepinephrine, and EDTA. Other hormones may be suitable examples of mediators, but the mediator is not limited to hormones.

Finally, a characteristic affected by the blood and/or blood components in the region containing interstitial fluid is monitored 30 which correlates with in vitro coagulation assays such as prothrombin time. The blood and/or blood components which leak out of the capillary 24 as a result of the mediator and/or local damage by the microneedle will be catalyzed to coagulate by the traumatized tissue or naturally present coagulation activators at a rate dependent on the concentration of coagulation factors present. As a result of the increased vascular permeability of the capillaries and the formation of endothelial gaps, the concentration of coagulation factors in the region tested will correlate to the concentrations of these factors in the blood stream. As coagulation occurs, viscosity, physical, optical, electrical, or chemical properties of the affected region may change. These changes may be monitored over time with suitable sensing elements. One suitable way to measure physical properties such as stiffness or viscosity is to oscillate or move a mechanical sensing device and measure the strain, Young's modulus, or mechanical impedance. This may be done using electrostatic actuators driven by a controlled voltage or magnetic actuators driven by a controlled current. Other characteristics such as electrical impedance may be affected by clotting. Two electrode structures can be inserted into the patient to measure impedance in the region being coagulated. These electrode structures can include microneedles which are used to penetrate the stratum corneum. Real and imaginary components of the impedance in the region being coagulated can be monitored as a function of frequency to track capacitance and conductivity changes due to the clotting process. Frequency analysis of the impedance may be used to monitor charge transport and mechanical changes that occur during the clotting process. The time interval over which these changes occur may be correlated to the prothrombin time measured in the in-vitro assay.

Another change in a characteristic of the blood in the interstitial fluid which may be monitored is capacitance change. Two microneedles spaced apart in the clot region will have a certain capacitance between them. A bias voltage applied to the microneedles during a capacitance measurement will create an attractive force between the microneedles. Before the blood clots, the microneedles will tend to move towards each other due to this attractive force, causing the microneedles to be spaced apart at a first distance. As the blood starts to clot, and after a voltage is applied again, the clotted blood will tend to keep the microneedles from moving towards each other, thereby changing the spacing of the microneedles compared to an earlier measurement. Such a change in microneedle or sensor spacing will cause a change in capacitance to be noted and may be used to indicate that a clot has occurred. The time where the change in capacitance occurred may be the prothrombin time or correlated to the prothrombin time. Alternatively, the applied voltage may be used to measure impedance. For simplicity, capacitance measurements are referred to in some of the following embodiments. It should be understood, however, that impedance could also be measured.

Figure 2B:
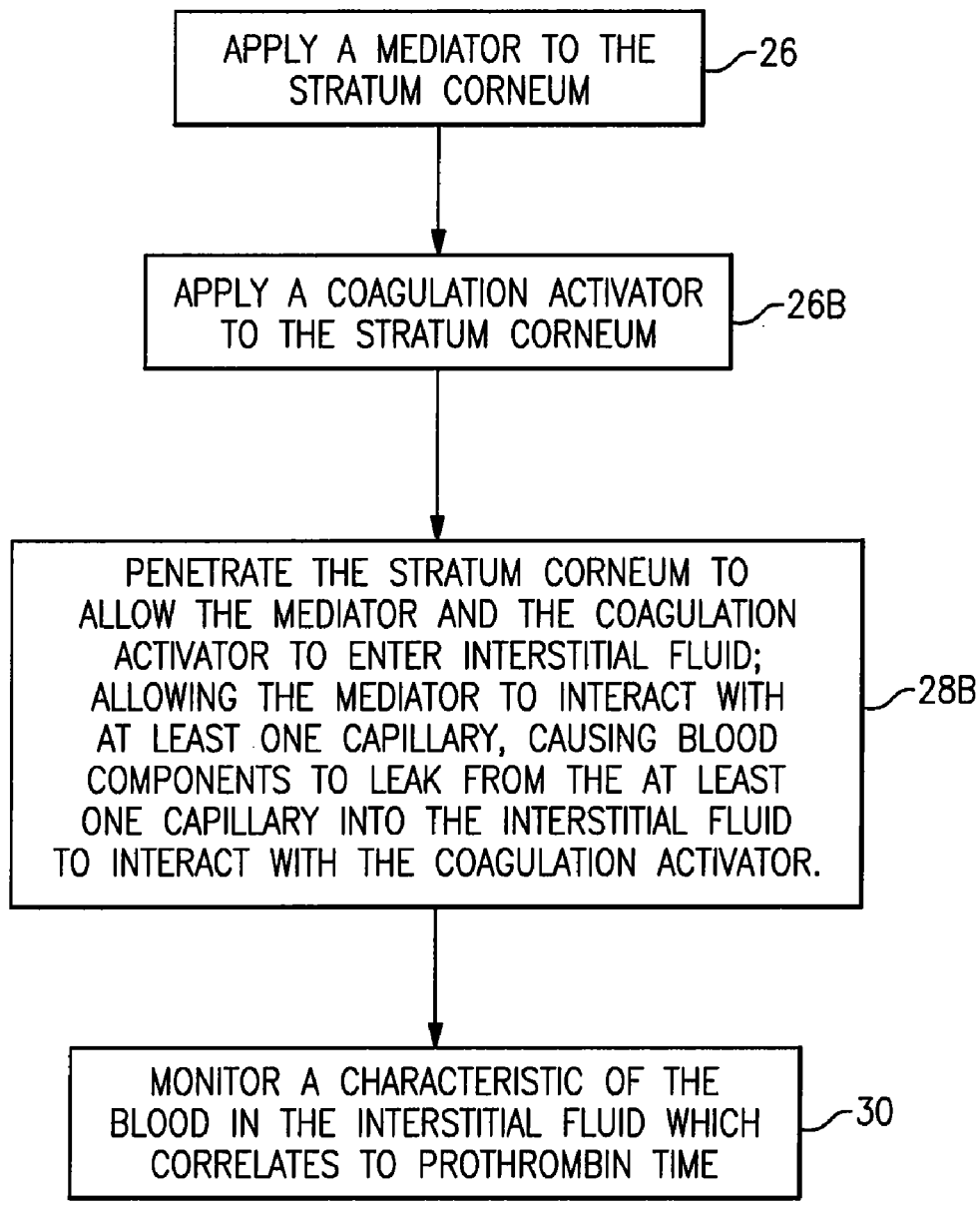
FIG. 2B illustrates another embodiment of a method of determining a prothrombin time.

The method embodied in FIG. 2A is suitable for use with a mediator which will cause sufficient tissue damage to the skin, the vascular tissue, the blood cells, or other tissue which the mediator contacts, resulting in the damaged tissue being able to initiate the coagulation cascade effect. In some situations, however, the mediator may not traumatize the tissue, and therefore, the coagulation cascade would not be initiated and a PT determination could not be made. In these situations, as well as others, it may be desirable to have an alternate method which allows the introduction of a coagulation activator to initiate the coagulation cascade in the blood and/or blood components which are released into the region containing interstitial fluid by the interaction of the mediator with the at least one capillary. FIG. 2B illustrates an embodiment of such a method of determining a prothrombin time. A mediator is applied 26 to the stratum corneum 20. A mediator is a substance or structure that mediates a specific response in a bodily tissue. As used here, the mediator is a substance which is configured to increase microvascular permeability when contacting the at least one capillary 24, thereby allowing blood components such as plasma, proteins, macromolecules, and blood cells to leak out of the at least one capillary 24 into the interstitial fluid 22. The mechanism responsible for this phenomenon is believed to be the creation of gaps in capillary walls caused by contraction of endothelial cells composing the capillary walls.

The mediator may be applied 26 to the stratum corneum 20 in a variety of ways. For example, the mediator may be applied in a liquid form to the stratum corneum 20. The mediator may also be applied to the stratum corneum 20 by touching a microneedle coated with the mediator to the stratum corneum 20. The mediator may be dry coated or liquid-coated onto the microneedle.

A coagulation activator is applied 26B to the stratum corneum. A coagulation activator is a substance which can trigger or initiate a coagulation cascade if it contacts the appropriate clotting factors which may be found in the blood. Suitable examples of coagulation activators include, but are not limited to, thromboplastin, glyco-proteins, phospholipids, and lipoproteins. The activator may be applied to the stratum corneum in a variety of ways. For example, the coagulation activator may be applied in a liquid form to the stratum corneum 20. The coagulation activator may also be applied to the stratum corneum 20 by touching a microneedle coated with the coagulation activator to the stratum corneum 20. The coagulation activator may also be dry coated or liquid-coated onto the microneedle. In the case where one or microneedles are coated with both a mediator and a coagulation activator, even if the activator coating physically touches the stratum corneum, while the mediator lies behind this activator on the microneedle, or visa versa, then it should be understood that both the mediator and the activator are still being applied to the stratum corneum just the same as if both were in physical contact with the stratum corneum.

Next, the stratum corneum 20 is penetrated 28B to allow the mediator and the coagulation activator to enter the region containing interstitial fluid 22; allowing the mediator to interact with at least one capillary 24, causing blood and/or blood components to leak from the at least one capillary 24 into the region containing interstitial fluid 22. When the blood and/or blood components leak into the region containing interstitial fluid, the blood and/or blood components can interact with the coagulation activator. At least one microneedle may be used to penetrate the stratum corneum 20. The microneedle may be preferably sized to penetrate the stratum corneum 20 while not extending down into nerve tissue in order to minimize the discomfort and pain for a subject. In some embodiments, the microneedle may cause minor damage to local capillaries resulting in additional leakage of blood and/or blood components such as plasma, proteins, macromolecules, and blood cells. A microneedle may have a height of about 50-1000 microns and a tip dimension from submicron to about 80 microns in order to penetrate a subject's skin, although other embodiments may have other dimensions. Other embodiments may use other penetrating devices besides a microneedle.

The mediator is chosen to interact with the at least one capillary 24 to cause blood and/or blood components to leak from the at least one capillary 24. The mediator can do this, for example, by increasing the microvascular permeability of the capillary walls. One example of a suitable mediator which may have this effect is histamine. Other suitable examples of mediators may be serotonin, norepinephrine, and EDTA. Other hormones may be suitable examples of mediators, although it should be understood that the mediator is not limited to being a hormone.

Finally, a characteristic affected by the blood and/or blood components in the region containing interstitial fluid is monitored 30 which correlates with in vitro coagulation assays such as prothrombin time. The blood and/or blood components which leak out of the capillary 24 as a result of the mediator and/or local damage by the microneedle will be catalyzed to coagulate by the coagulation activator at a rate dependent on the concentration of coagulation factors present. The coagulation activator is chosen such that it promotes the formation of clots when in the presence of coagulation factors. An example of an activator is a substance called prothrombin activator which catalyzes the conversion of prothrombin (typically inactive) into thrombin. Examples of prothrombin activators include proteins such as staphylocoagulase, thromboplastin, and others. Once thrombin is created, it converts fibrinogen into fibrin and linked fibrin filaments which provide a fibrous mass able to trap blood cells and induce clotting.

As a result of the increased vascular permeability of the capillaries and the formation of endothelial gaps, the concentration of coagulation factors in the region tested will correlate to the concentrations in the blood stream. As coagulation occurs, viscosity, physical, optical, electrical, or chemical properties of the affected region will change. These changes may be monitored over time with suitable sensing elements. One suitable way to measure physical properties such as stiffness or viscosity is to oscillate or move a mechanical sensing device and measure the strain, Young's modulus, or mechanical impedance. This may be done using electrostatic actuators driven by a controlled voltage or magnetic actuators driven by a controlled current. Other characteristics such as electrical impedance may be affected by clotting. Two electrode structures can be inserted into the patient to measure impedance in the region being coagulated. These electrode structures can include microneedles which are used to penetrate the stratum corneum. Real and imaginary components of the impedance in the region being coagulated can be monitored as a function of frequency to track capacitance and conductivity changes due to the clotting process. Frequency analysis of the impedance may be used to monitor charge transport and mechanical changes that occur during the clotting process. The time interval over which these changes occur may be correlated to the prothrombin time measured in the in-vitro assay.

FIGS. 3A1-3D1 schematically illustrate one embodiment of a system 32 for measuring prothrombin time and steps in the prothrombin time measuring process according to the method embodied in FIG. 2A. The illustrated system 32 has a first microneedle 34 and a second microneedle 36 which are part of a microneedle array 38. Other embodiments may have fewer microneedles or more microneedles. The microneedles 34, 36 in this embodiment are preferably made from a conductive or semiconductive material which can be circuited to allow a voltage potential to be placed across the two microneedles 34, 36. Suitable techniques for forming the microneedles include micromechanical fabrication techniques and/or semiconductor fabrication techniques, including etching processes. The microneedles 34, 36 are coupled to a processor 40 which is configured to determine a coagulation change in blood and/or blood components in a region around (in this case between) the microneedles 34, 36. This determination will be discussed in further detail with regard to FIG. 3D1. The processor 40 may include a microprocessor, a computer, an application specific integrated circuit (ASIC), digital components, analog components, any combination thereof, or equivalent thereof. A user interface 42 is coupled to the processor 40 in order to enable the processor 40 to display test results to a user. A mediator 44 is coated onto the first microneedle 34. In other embodiments, the mediator may be coated onto the tissue, rather than onto the microneedle. Other embodiments may have the mediator 44 coated on more than one microneedle. As discussed above, a suitable mediator 44 is configured to increase microvascular permeability. In FIG. 3A1, the mediator 44 is first applied 46 to the stratum corneum 20 when the microneedle 34 contacts the stratum corneum 20.

In FIG. 3B1, the microneedles 34, 36 have been actuated through the stratum corneum 20 and into a region containing interstitial fluid 22. A suitable actuator (not shown) may be a mechanical plunger, a manual actuator, a spring loaded actuator, a piezoelectric actuator, or an electro-mechanical actuator, such as a solenoid. As a result of the actuation, the mediator 44 contacts the region containing interstitial fluid 22. In embodiments where the mediator is a liquid applied to the skin prior to the penetration by the microneedles, the microneedles create pathways for the liquid mediator to reach the region containing interstitial fluid. In FIG. 3C1, the mediator 44 enters 48 the region containing interstitial fluid 22 by dissolving in the region containing interstitial fluid 22. The mediator 44 interacts 50 with the capillary 24.

As a result of the interaction between the mediator 44 and the capillary 24, the microvascular permeability of the capillary 24 is increased, causing blood and/or blood components 52 to leak 54 from the capillary 24 into the region containing interstitial fluid as illustrated in FIG. 3D1. Since the mediator 44 was introduced to the region containing interstitial fluid 22 by the microneedles 34, 36, the blood and/or blood components 52 should enter the region containing interstitial fluid 22 in the area around the microneedles 34, 36. Some of the blood and/or blood components 52 may enter the area between 56 the microneedles 34, 36. As mentioned previously, the blood and/or blood components 52 will begin to clot at a rate dependent on the concentration of clotting factors present. The processor 40 may apply a voltage across the microneedles 34, 36 at various times to measure the capacitance between the microneedles 34, 36. The capacitance may change over time, as discussed above. This change in capacitance may be correlated to the formation of a clot, which in turn may be correlated to a prothrombin time. The amount of bleeding from such a test should be minimal, for example, on par with the bleeding which occurs as a result of a mosquito bite. The process should be relatively painless since the penetration of the subject's skin preferably does not pass down into the nerve regions of the tissue. Thus, a simple, quick, and non-invasive PT test procedure is enabled by this system. The processor can be configured to make the test determinations automatically, thereby reducing the need for health professional time to perform the test, and even making it possible for someone to test their own PT time themselves.

FIGS. 3A2-3D2 schematically illustrate one embodiment of a system 32 for measuring prothrombin time and steps in the prothrombin time measuring process according to the method embodied in FIG. 2B. The illustrated system 32 has a first microneedle 34 and a second microneedle 36 which are part of a microneedle array 38. Other embodiments may have fewer microneedles or more microneedles. The microneedles 34, 36 in this embodiment are preferably made from a conductive or semiconductive material which can be circuited to allow a voltage potential to be placed across the two microneedles 34, 36. Suitable techniques for forming the microneedles include micromechanical fabrication techniques and/or semiconductor fabrication techniques, including etching processes. The microneedles 34, 36 are coupled to a processor 40 which is configured to determine a coagulation change in blood and/or blood components in a region around (in this case between) the microneedles 34, 36. This determination will be discussed in further detail with regard to FIG. 3D2. The processor 40 may include a microprocessor, a computer, an application specific integrated circuit (ASIC), digital components, analog components, any combination thereof, or equivalent thereof. A user interface 42 is coupled to the processor 40 in order to enable the processor 40 to display test results to a user. A mediator 44 is coated onto the first microneedle 34. In other embodiments, the mediator may be coated onto the tissue, rather than onto the microneedle. Other embodiments may have the mediator 44 coated on more than one microneedle. As discussed above, a suitable mediator 44 is configured to increase microvascular permeability. A coagulation activator 45 is coated onto the second microneedle 36. In other embodiments, the coagulation activator may be coated onto the tissue, rather than onto the microneedle. Other embodiments may have the coagulation activator 45 coated onto more than one microneedle. Still other embodiments may have the coagulation activator 45 and the mediator 44 coated onto the same microneedle or multiple microneedles. As discussed above, a suitable coagulation activator 45 is configured or selected to initiate a coagulation cascade. In FIG. 3A2, the mediator 44 and the coagulation activator 35 are first applied 46 to the stratum corneum 20 when the microneedles 34, 36 contact the stratum corneum 20.

In FIG. 3B2, the microneedles 34, 36 have been actuated through the stratum corneum 20 and into a region containing interstitial fluid 22. A suitable actuator (not shown) may be a mechanical plunger, a manual actuator, a spring loaded actuator, a piezoelectric actuator, or an electro-mechanical actuator, such as a solenoid. As a result of the actuation, the mediator 44 and the coagulation activator 45 contact the region containing interstitial fluid 22. In embodiments where the mediator 44 is a liquid applied to the skin prior to the penetration by the microneedles, the microneedles create pathways for the liquid mediator to reach the region containing interstitial fluid. Similarly, in embodiments where the coagulation activator 45 is a liquid applied to the skin prior to the penetration by the microneedles, the microneedles create pathways for the liquid coagulation activator to reach the region containing interstitial fluid. In FIG. 3C2, the mediator 44 enters 48 the region containing interstitial fluid 22 by dissolving or diffusing in the region containing interstitial fluid 22. Similarly, the coagulation activator 45 enters 49 the region containing interstitial fluid 22 by dissolving in the region containing interstitial fluid 22. The mediator 44 interacts 50 with the capillary 24.

As a result of the interaction 50 between the mediator 44 and the capillary 24, the microvascular permeability of the capillary 24 is increased, causing blood and/or blood components 52 to leak 54 from the capillary 24 into the region containing interstitial fluid 22 as illustrated in FIG. 3D2. Since the mediator 44 was introduced to the region containing interstitial fluid 22 by the one or more microneedles 34, 36, the blood and/or blood components 52 should enter the region containing interstitial fluid 22 in the area around the microneedles 34, 36. Some of the blood and/or blood components 52 may enter the area between 56 the microneedles 34, 36. The blood and/or blood components 52 can come into contact with the coagulation activator 45 in the region containing interstitial fluid. The blood and/or blood components 52 will begin to clot at a rate dependent on the concentration of coagulation activator 45 present. The processor 40 may apply a voltage across the microneedles 34, 36 at various times to measure the capacitance between the microneedles 34, 36. The capacitance may change over time, as discussed above. This change in capacitance may be correlated to the formation of a clot, which in turn may be correlated to a prothrombin time. The amount of bleeding from such a test should be minimal, for example, on par with the bleeding which occurs as a result of a mosquito bite. The process should be relatively painless since the penetration of the subject's skin preferably does not pass down into the nerve regions of the tissue. Thus, a simple, quick, and non-invasive PT test procedure is enabled by this system. The processor can be configured to make the test determinations automatically, thereby reducing the need for health professional time to perform the test, and even making it possible for someone to test their own PT time themselves.

Figure 4A:
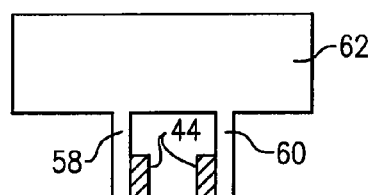
FIGS. 4A-4D schematically illustrate other embodiments of microneedle arrays which may be used in a system for monitoring prothrombin time.

FIGS. 4A-4D schematically illustrate other embodiments of microneedle arrays which may be used in a system for measuring prothrombin time. In the embodiment of FIG. 4A, both microneedles 58, 60 are coated with a mediator 44. Although the microneedles 58, 60 in this embodiment are schematically illustrated as having the mediator 44 coated on only one side of the microneedles, in other embodiments, the mediator 44 may be coated on multiple sides of the microneedles. This may be desirable for manufacturing purposes, since when coating the microneedle array 62, it may be desirable to dip the entire array in the mediator, rather than have to try to place the mediator on only a specific microneedle. In the event that specific microneedles need to be coated with a mediator, a pipette array or an inkjet style dispenser may be used to apply the mediator to specific locations on the microneedle array.

Figure 4C:
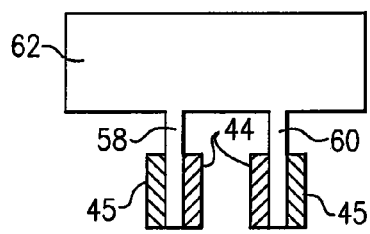
Figure 4B:
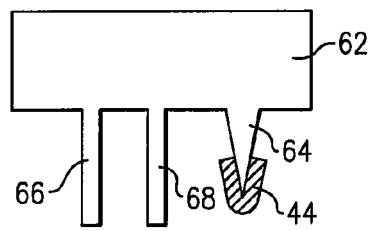

As FIG. 4B illustrates, some embodiments may use a separate microneedle 64 to deliver the mediator 44 to the region containing interstitial fluid. In this case, the microneedles 66, 68 which will measure the changing characteristic which correlates to blood clotting do not deliver the mediator 44, but are in the vicinity of the delivery microneedle 64 so as to be able to come into contact with blood components released by the mediator 44. It should also be noted that the microneedles of any of the embodiments discussed in this specification, as well as their equivalents, may come in a variety of sizes and shapes. For example, microneedles may have a round cross-section, a square cross-section, a triangular cross-section, a varying cross-section, or any other cross-section deemed appropriate for penetrating the stratum corneum and making a measurement.

In the embodiment of FIG. 4C, microneedles 58, 60 are each coated with a mediator 44 and a coagulation activator 45. Although the microneedles 58, 60 in this embodiment are schematically illustrated as having the mediator 44 and the coagulation activator 45 coated on separate sides of the microneedles, in other embodiments, the mediator 44 and the coagulation activator 45 may be coated on the same side of the microneedles. In other embodiments, the coagulation activator 45 may first be coated on top of the microneedle and then the mediator 44 may be coated on top of the coagulation activator 44 and visa versa. This may be desirable for manufacturing purposes, since when coating the microneedle array

62, it may be desirable to dip the entire array in the coagulation activator and then the mediator, rather than have to try to place the coagulation activator and the mediator on only a specific microneedle. In the event that specific microneedles need to be coated with a coagulation activator and a mediator, a pipette array or an inkjet style dispenser may be used to apply the coagulation activator and the mediator to specific locations on the microneedle array.

Figure 4D:
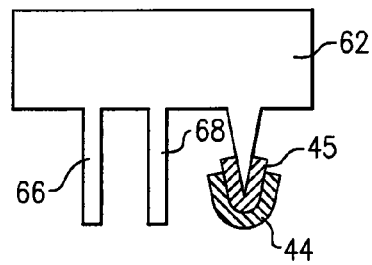

As FIG. 4D illustrates, some embodiments may use a separate microneedle 64 to deliver the mediator 44 and the coagulation activator 45 to the region containing interstitial fluid. In this case, the microneedles 66, 68 which will measure the changing characteristic which correlates to blood clotting do not deliver the mediator 44 and the coagulation activator 45, but are in the vicinity of the delivery microneedle 64 so as to be able to come into contact with blood and/or blood components released by the mediator 44. Other embodiments may have separate delivery microneedles for the mediator and the coagulation activator. It should also be noted that the microneedles of any of the embodiments discussed in this specification, as well as their equivalents, may come in a variety of sizes and shapes. For example, microneedles may have a round cross-section, a square cross-section, a triangular cross-section, a varying cross-section, or any other cross-section deemed appropriate for penetrating the stratum corneum and making a measurement.

Figure 5A:
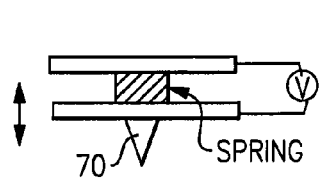
FIGS. 5A-5C schematically illustrate embodiments of systems for monitoring a prothrombin time using a single microneedle.
Figure 5B:
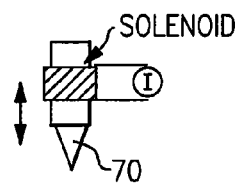
Figure 5C:
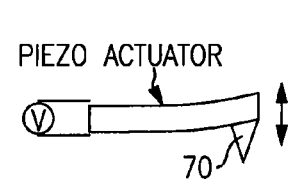

As FIGS. 5A-5C illustrate, some embodiments may use only one microneedle 70. For simplicity, the mediator and the optional coagulation activator coatings are not shown in FIGS. 5A-5C. This single microneedle 70 may be driven by an oscillating voltage, and the mechanical impedance can be measured. In the embodiments of FIGS. 5A-5C, a mechanical transducer moves an incremental distance determined by an applied voltage or current. In the case of FIG. 5A, the transducer is a capacitor with a DC or AC voltage applied. In the case of FIG. 5B, the transducer is a solenoid with AC or DC current applied. In the case of FIG. 5V, the transducer is a piezo transducer with an AC or DC voltage applied.

Although a processor has been illustrated in the preceding embodiments as the device being used to monitor a characteristic of the blood and/or blood components in the region containing interstitial fluid which correlates to PT time, other embodiments may have a more broad monitoring system which monitors the characteristic. In some embodiments, the monitoring system could be manual and would subjectively or objectively characterize a size of a wheal resulting from the clotted blood and/or blood components in the region containing interstitial fluid. Blood and/or blood components which take longer to clot may produce a larger wheal. The objective characterization could include a diameter or area measurement. The subjective characterization could include a ranking based on previous measurements (smaller, larger, the same) or a classification based on a visual comparison with example pictures or pictorial representation of various wheal sizes, for example on a reference card provided to a patient by a healthcare provider or as part of a PT test kit.

In other embodiments, the monitoring system could include an image capturing system coupled to a processor for automated or semi-automated visual analysis of the characteristics of the coagulated wheal which results from a test. The visual-based results could be used on their own or in conjunction with the PT measurements described in the embodiments above.

Figure 6:
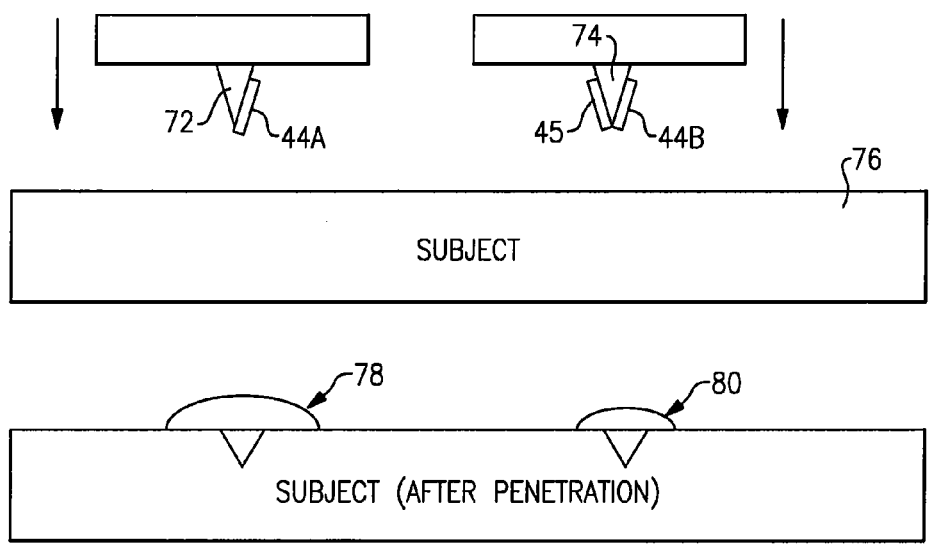
FIG. 6 schematically illustrates an embodiment of a system for monitoring prothrombin time.

FIG. 6 schematically illustrates another embodiment of a system for measuring prothrombin time or a characteristic which correlates to prothrombin time. In this case, a first microneedle 72 is coated with just the vascular permeability mediator 44A. A second microneedle 74 is coated with both the vascular permeability mediator 44B as well as a coagulation activator 45. The two needles 72, 74 are separated by a sufficient distance so as to avoid diffusion (mixing) between the coagulation activator 45 coated on the second microneedle 74 and the vascular permeability mediator 44A coated on the first microneedle 72. The distance between the first and second microneedles 72, 74 may be greater than 5 mm, and preferably greater than 15 mm in some embodiments, however lesser or greater spacings may be used, depending on the embodiment and the mediator and coagulation activator being used. After the microneedles 72, 74 are inserted into the subject 76 a first wheal 78 corresponding to the first microneedle 72 will be produced. Similarly, a second wheal 80 corresponding to the second microneedle 74 will be produced. The second wheal 80, associated with the second microneedle 74 containing the coagulation activator 45 should have a reduced diameter (clotting reduces the amount of blood and/or blood components that escape the blood vessel). The difference in size between the wheals 78, 80 produced by the microneedles 72, 74 is a measure of blood's ability to coagulate and may be correlated with in-vitro (e.g.) PT coagulation assays. If the clotting ability of blood is low, the size difference between the two wheals is small. If the clotting ability of blood is high, the size difference between the two wheals is large. The measurement can be done visually by a technician by measuring the difference in wheal sizes or by a monitor (digital capture system and image analysis software) and user interface.

FIG. 7 schematically illustrates another embodiment of a system 82 for measuring a prothrombin time. As described in previous embodiments, one or more microneedles 84 may be coated with at least a mediator to induce the leakage of blood and/or blood components 86 from at least one capillary 24 into a region containing interstitial fluid 22. Although the embodiment of FIG. 7 illustrates two microneedles 84, it should be understood that other embodiments may have one or more microneedles 84. As also described in previous embodiments, the one or more microneedles 84 may also be coated with a coagulation activator which can operate as described. For simplicity in FIG. 7, any mediator and coagulation activator have not been shown.

The blood clotting which occurs with the blood and/or blood components 86 may be imaged by an external image sensor or camera 88 configured with a suitable source of illumination 90. A suitable source of illumination 90 may include a lamp with a suitable optical filter, an infrared LED, or an infrared laser. If the one or more microneedles 84 and/or the microneedle substrate 92 are transparent or semi-transparent, then the imaging process can occur with the one or more microneedles 84 still in-place in the region containing interstitial fluid or on the stratum corneum 20. In such transparent or semi-transparent embodiments, the microneedles 84 and/or the microneedle substrate 92 may be made, for example, from quartz, glass, or plastic. In other embodiments, the one or more microneedles 84 may be retracted and/or moved out of the imaging path to allow the camera 88 to have a more direct view of the stratum corneum 20.

Even though the leaked blood and/or blood components 86 which will be monitored for clotting are substantially below the surface of the skin, it is known in the art that the penetration depth of light through skin increases with wavelength, enabling the imaging of structures or features below the skin surface at, for example, near-infrared (NIR) wavelengths. As the blood and/or blood components 86 clot, they may scatter more NIR light and become visible to the camera system 88. As just one example, the camera system 88 may be a digital camera microscopy system having a CCD or CMOS sensor with reasonable quantum efficiency from the visible into the near infrared for wavelengths up to about 1000 nm. A non-limiting example of suitable NIR imaging wavelengths is between 700 nm and 1000 nm.

FIGS. 8A-8F schematically illustrate another embodiment of a system for monitoring prothrombin time and steps in the prothrombin time monitoring process. As FIG. 8A schematically illustrates, in this embodiment, the system has at least one microneedle 94 which is coated with a mediator 96. The properties of a suitable mediator 96 have been discussed above with regard to other embodiments. As FIG. 8B schematically illustrates, the at least one microneedle 94 penetrates the stratum corneum to allow the mediator 96 to enter 98 a region containing interstitial fluid 100. As FIG. 8C schematically illustrates, the at least one microneedle 94 is extracted 102. Although the extracted microneedle 94 is illustrated as having no mediator left on the needle, in actual practice, the extracted microneedle may have some remaining mediator on it. As previously described, the mediator 96 will interact with at least one capillary, causing blood and/or blood components to leak from the at least one capillary into the region containing interstitial fluid 98. After a period of time corresponding to an interval required for the mediator to promote the leakage of blood and/or blood components 104 out of the at least one capillary at least one other microneedle 106 is inserted into a wheal region 108 caused by the leaked blood and/or blood components 104 as schematically illustrated in FIG. 8D. The at least one other microneedle 106 is preferably coated with a coagulation activator 110 which interacts 112 with the blood and/or blood components 104. As FIG. 8E schematically illustrates, the at least one other microneedle 106 may be coupled to a processor (not shown) for monitoring a characteristic of the blood and/or blood components, as coagulation occurs, which correlates to prothrombin time as previously described. Although the at least one other microneedle 106 in this embodiment was illustrated as being coated with a coagulation activator 110, in other embodiments, a coagulation activator may not be necessary, since the blood and/or blood components may tend to coagulate on their own. Finally, as FIG. 8F schematically illustrates, the at least one other microneedle 106 may be extracted 114 from the subject. In other embodiments, the needle coated with the coagulation activator and the sensing needle could be different needles. The needle coated with the coagulation activator and/or the sensing needle (depending on the embodiment) could be inserted at the location where the needle with the mediator was inserted, or they may be inserted at a nearby location.

Figure 9A:
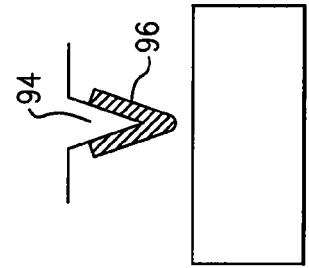
FIGS. 9A-9E schematically illustrate another embodiment of a system for monitoring prothrombin time and steps in the prothrombin time monitoring process.
Figure 9B:
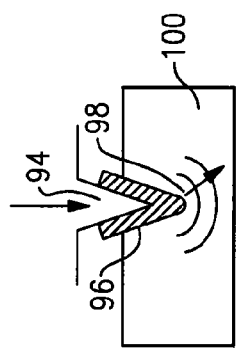
Figure 9C:
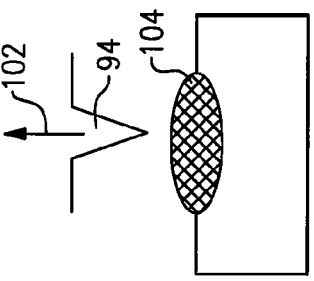
Figure 9D:
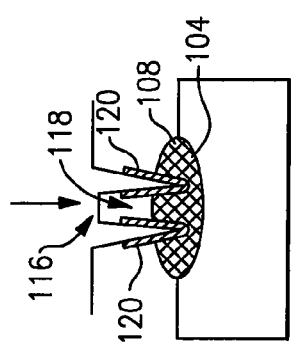
Figure 9E:
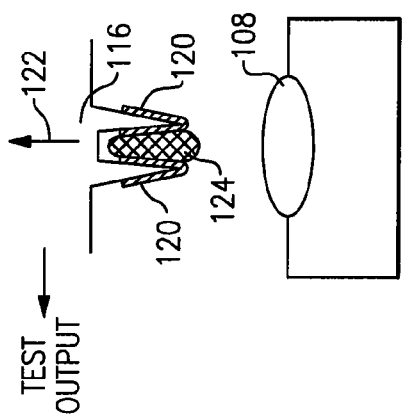

FIGS. 9A-9E schematically illustrate another embodiment of a system for monitoring prothrombin time and steps in the prothrombin time monitoring process. As FIG. 9A schematically illustrates, in this embodiment, the system has at least one microneedle 94 which is coated with a mediator 96. The properties of a suitable mediator 96 have been discussed above with regard to other embodiments. As FIG. 9B schematically illustrates, the at least one microneedle 94 penetrates the stratum corneum to allow the mediator 96 to enter 98 a region containing interstitial fluid 100. As FIG. 9C schematically illustrates, the at least one microneedle 94 is extracted 102. Although the extracted microneedle 94 is illustrated as having no mediator left on the needle, in actual practice, the extracted microneedle may have some remaining mediator on it. As previously described, the mediator 96 will interact with at least one capillary, causing blood and/or blood components to leak from the at least one capillary into the region containing interstitial fluid 98. After a period of time corresponding to an interval required for the mediator to promote the leakage of blood and/or blood components 104 out of the at least one capillary, a sampling microneedle 116 is inserted into a wheal region 108 caused by the leaked blood and/or blood components 104 as schematically illustrated in FIG. 9D. The sampling microneedle 116 is configured to withdraw liquid from the wheal region 108. Suitable examples of sampling microneedles include, but are not limited to, microneedles having an orifice, a cannula, or a porous coating on the microneedle. The sampling microneedle 116 in the embodiment of FIG. 9D has an example of an orifice 118. A coagulation activator 120 is also coated on the sampling microneedle 116 such that the coagulation activator 120 will contact the fluid withdrawn from the wheal region 108. As FIG. 9E schematically illustrates, sampling microneedle 116 is removed 122 from the subject along with its sampled fluid 124 having blood and/or blood components. The sampling microneedle 116 may be coupled to a processor (not shown) for monitoring a characteristic of the blood and/or blood components, as coagulation occurs, which correlates to prothrombin time as previously described.

FIG. 10 schematically illustrates a system 126 for prescribing a dosage of a blood thinner for a patient 128. The patient 128 interacts 130 with a microneedle and mediator 132, for example, as described in the preceding embodiments. Through this interaction, blood and/or blood components are released from at least one capillary. A characteristic sensor 134 measures a characteristic of the blood and/or blood components and passes this information to a processor 136. As described above, the characteristic of the blood and/or blood component may be an optical, physical, or electrical characteristic, depending on the type of characteristic sensor 134 being used.

The processor 136 may be a computer, laptop, notebook, microprocessor, application specific integrated circuit (ASIC), digital components, analog components, any combination thereof, or equivalent thereof. The processor 136 may also be self-contained or distributed among multiple processing components. In embodiments with distributed multiple processing components, the distributed components may be local, remote, or any combination thereof. The processor 136 can have one or more storage devices such as, but not limited to, a read-only-memory (ROM), a random access memory (RAM), a magnetic hard drive, an optical hard drive, a CD drive, and a DVD drive on which machine-readable instructions may be stored. The processor 136 can execute such instructions.

In this embodiment, the processor 136 is configured to correlate a sensed characteristic to a PT time 138. This sensed PT time can optionally be communicated 140 to the patient 128 via a user interface 142 coupled to the processor 136. The processor 136 may also store patient characteristics 144 and blood thinner dosing rules 146. The patient characteristics 144 may be entered by the patient 128 via the user interface 142. Optionally, the patient characteristics 144 may be entered by a medical professional 148. PT times may optionally be stored 150 with the patient characteristics 144 if it is desired to store historical PT time data for the patient in order, for example, to look at PT time trends. The processor 136 can come configured with a set of blood thinner dosing rules 146 or the medical professional 148 may optionally enter a set of blood thinner dosing rules 146 for the patient 128.

The processor 136 is further configured to determine a current recommended blood thinner dosage 152 based at least on patient characteristics 144, blood thinner dosing rules 146, and a PT time 154. The recommended blood thinner dosage may then be communicated 156 to the patient 128 via the user interface 142.

Having thus described several embodiments of the claimed invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of the processing elements or sequences, or the use of numbers, letters, or other designations therefore, is not intended to limit the claimed processes to any order except as may be specified in the claims. Accordingly, the claimed invention is limited only by the following claims and equivalents thereto.

What is claimed is:

1. A method of determining a prothrombin time, comprising:
    applying a mediator to a stratum corneum;
    penetrating the stratum corneum to allow the mediator to enter a region containing interstitial fluid and interact with at least one capillary, causing blood and/or blood components to leak from the at least one capillary into the region containing interstitial fluid;
    measuring a characteristic affected by the blood and/or blood components in the region containing interstitial fluid which correlates to the prothrombin time; and
    applying a coagulation activator to the stratum corneum, and wherein penetrating the stratum corneum also allows the coagulation activator to enter the region containing interstitial fluid, and the blood and/or blood components which have been caused to leak from the at least one capillary into the region containing interstitial fluid can interact with the coagulation activator.

2. The method of claim 1, wherein applying the mediator to the stratum corneum comprises applying the mediator in a liquid form to the stratum corneum.

3. The method of claim 1, wherein applying the mediator to the stratum corneum comprises bringing a microneedle coated with the mediator into contact with the stratum corneum.

4. The method of claim 3, further comprising dry-coating the mediator onto the microneedle.

5. The method of claim 3, further comprising liquid-coating the mediator onto the microneedle.

6. The method of claim 1, wherein a microneedle is used to penetrate the stratum corneum.

7. The method of claim 1, wherein the mediator is a histamine.

8. The method of claim 1, wherein the mediator is selected from the group consisting of serotonin, norepinephrine, and EDTA.

9. The method of claim 1, wherein the measured characteristic affected by the blood and/or blood components in the region containing interstitial fluid which correlates to the prothrombin time is selected from the group consisting of:
    a viscosity;
    a physical property;
    an optical property;
    an electrical property;
    a chemical property;
    a stillness;
    a strain;
    a mechanical impedance;
    an electrical impedance; and
    a capacitance.

10. The method of claim 1, wherein the coagulation activator is selected from the group consisting of thromboplastin, staphylocoagulase, glycoproteins, phospholipids, and lipoproteins.

11. A system for measuring prothrombin time, comprising:
    a mediator;
    one or more microneedles;
    a computing device coupled to the one or more microneedles and configured to determine a coagulation change in blood or blood components in a region around the one or more microneedles after the one or more microneedles penetrate a stratum corneum wherein the computing device is configured to determine the coagulation change in blood or blood components in the region around the one or more microneedles by applying a voltage across a plurality of microneedles and monitoring a capacitance change between the microneedles.

12. The system of claim 11, wherein the mediator is coated onto at least one of the microneedles.

13. The system of claim 11, further comprising an actuator configured to penetrate the one or more microneedles through the stratum corneum and into a region containing interstitial fluid.

14. The system of claim 11, further comprising an image capturing system configured for automated or semi-automated image analysis of one or more coagulated wheals which result following the penetration of the stratum corneum.

15. A system for prescribing a dosage of blood thinner for a patient, comprising:
    a mediator;
    one or more microneedles;
    a computing device coupled to the one or more microneedles and configured to:
    determine a coagulation change in blood or blood components in a region around the one or more microneedles after the one or more microneedles penetrate a stratum corneum:
    store one or more patient characteristics;
    store one or blood thinner dosing rules; and
    determine a recommended blood thinner dosage based on the one or more patient characteristics, the one or more blood thinner dosing rules, and the determined coagulation change.

16. A system for measuring prothrombin time, comprising:
    a mediator;
    one or more microneedles;
    a computing device coupled to the one or more microneedles and configured to determine a coagulation change in blood or blood components in a region around the one or more microneedles after the one or more microneedles penetrate a stratum corneum; and
    a coagulation activator.

17. The system of claim 16, wherein the mediator is coated onto at least one of the microneedles.

18. The system of claim 16, further comprising an actuator configured to penetrate the one or more microneedles through the stratum corneum and into a region containing interstitial fluid.

19. The system of claim 16, wherein the coagulation activator is coated onto at least one of the microneedles.

20. The system of claim 16, further comprising an image capturing system configured for automated or semi-automated image analysis of one or more coagulated wheals which result following the penetration of the stratum corneum.

21. A system for measuring prothrombin time, comprising:
a mediator;
one or more microneedles;
a computing device coupled to the one or more microneedles and configured to determine a coagulation change in blood or blood components in a region around the one or more microneedles after the one or more microneedles penetrate a stratum corneum wherein the computing device's determination of the coagulation change in blood or blood components in a region around the one or more microneedles occurs while the needles are penetrating the stratum corneum.

22. The system of claim 21, wherein the mediator is coated onto at least one of the microneedles.

23. The system of claim 21, further comprising an actuator configured to penetrate the one or more microneedles through the stratum corneum and into a region containing interstitial fluid.

24. The system of claim 21, further comprising an image capturing system configured for automated or semi-automated image analysis of one or more coagulated wheals which result following the penetration of the stratum corneum.

* * * * *